(12) United States Patent
Greenhut et al.

(10) Patent No.: US 7,496,409 B2
(45) Date of Patent: Feb. 24, 2009

(54) IMPLANTABLE MEDICAL DEVICE SYSTEM AND METHOD WITH SIGNAL QUALITY MONITORING AND RESPONSE

(75) Inventors: Saul E. Greenhut, Aurora, CO (US); Robert W. Stadler, Shoreview, MN (US); Holly S. Vitense, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 321 days.

(21) Appl. No.: 11/392,065

(22) Filed: Mar. 29, 2006

(65) Prior Publication Data

US 2007/0239220 A1    Oct. 11, 2007

(51) Int. Cl.
*A61N 1/00* (2006.01)
(52) U.S. Cl. .................................................. 607/116
(58) Field of Classification Search .................. 607/116; 600/509, 521
See application file for complete search history.

(56) References Cited

U.S. PATENT DOCUMENTS

| | | | |
|---|---|---|---|
| 4,180,078 A | 12/1979 | Anderson | |
| 4,374,382 A | 2/1983 | Markowitz | |
| 4,548,209 A | 10/1985 | Wielders et al. | |
| 4,552,154 A | 11/1985 | Hartlaub | |
| 4,556,063 A | 12/1985 | Thompson et al. | |
| 4,567,892 A | 2/1986 | Plicchi | |
| 5,117,824 A | 6/1992 | Keimel et al. | |
| 5,127,404 A | 7/1992 | Wyborny et al. | |
| 5,163,427 A | 11/1992 | Keimel | |
| 5,176,137 A | 1/1993 | Erickson | |
| 5,188,105 A | 2/1993 | Keimel | |
| 5,193,535 A | 3/1993 | Bardy et al. | |
| 5,331,966 A | 7/1994 | Bennett et al. | |
| 5,354,316 A | 10/1994 | Keimel | |
| 5,464,434 A | 11/1995 | Alt | |
| 5,470,345 A | 11/1995 | Hassler et al. | |
| 5,522,860 A | 6/1996 | Molin et al. | |
| 5,593,431 A | 1/1997 | Sheldon | |
| 5,683,432 A | 11/1997 | Goedeke | |
| 5,752,976 A | 5/1998 | Duffin et al. | |
| 5,855,593 A | 1/1999 | Olson et al. | |
| 6,230,059 B1 | 5/2001 | Duffin | |
| 6,236,882 B1 | 5/2001 | Lee et al. | |
| 6,250,309 B1 | 6/2001 | Krichen et al. | |
| 6,393,316 B1 | 5/2002 | Gillberg et al. | |
| 6,418,346 B1 | 7/2002 | Nelson et al. | |
| 6,450,172 B1 | 9/2002 | Hartlaub et al. | |

(Continued)

FOREIGN PATENT DOCUMENTS

WO    WO2006049767 A    5/2006

OTHER PUBLICATIONS

International Search Report, PCT/US2007/063795, Sep. 26, 2007, 3 Pages.

*Primary Examiner*—George Manuel
(74) *Attorney, Agent, or Firm*—Michael C. Soldner

(57) ABSTRACT

An implantable medical device system and method are provided for monitoring the quality of signals sensed by a subcutaneously implanted device using subcutaneous electrodes. In one embodiment, the method includes selecting one or more sensing vectors; sensing signals from selected sensing vectors, determining a signal quality metric in response to a sensed signal, comparing the signal quality metric to a predetermined threshold, and generating a loss of signal quality response in response to the signal quality crossing the threshold.

25 Claims, 5 Drawing Sheets

U.S. PATENT DOCUMENTS

| | | |
|---|---|---|
| 6,480,745 B2 | 11/2002 | Nelson et al. |
| 6,482,154 B1 | 11/2002 | Haubrich et al. |
| 6,505,067 B1 | 1/2003 | Lee et al. |
| 6,512,940 B1 | 1/2003 | Brabec et al. |
| 6,522,915 B1 | 2/2003 | Ceballos et al. |
| 6,622,046 B2 | 9/2003 | Fraley et al. |
| 7,027,858 B2 * | 4/2006 | Cao et al. .................. 600/521 |
| 7,184,815 B2 * | 2/2007 | Kim et al. .................. 600/509 |
| 2002/0120307 A1 | 8/2002 | Jorgenson et al. |
| 2004/0049120 A1 | 3/2004 | Cao et al. |
| 2004/0092836 A1 | 5/2004 | Ritscher et al. |
| 2004/0106957 A1 | 6/2004 | Palreddy et al. |
| 2004/0230243 A1 | 11/2004 | Haefner et al. |
| 2004/0260350 A1 | 12/2004 | Brandsetter et al. |

\* cited by examiner

IMPLANTABLE MEDICAL DEVICE SYSTEM AND METHOD WITH SIGNAL QUALITY MONITORING AND RESPONSE

TECHNICAL FIELD

The invention relates generally to implantable medical devices, and, in particular, to a system and method for monitoring the quality of signals sensed by a subcutaneously implanted medical device.

BACKGROUND

Implantable medical devices are available for preventing or treating cardiac arrhythmias by delivering anti-tachycardia pacing therapies and electrical shock therapies for cardioverting or defibrillating the heart. Such a device, commonly known as an implantable cardioverter defibrillator or "ICD", senses a patient's heart rhythm and classifies the rhythm according to a number of rate zones in order to detect episodes of tachycardia or fibrillation. Rate zone classifications typically include normal sinus rhythm, tachycardia, and fibrillation. Both atrial and ventricular arrhythmias may be detected and treated.

Upon detecting an abnormal rhythm, the ICD delivers an appropriate therapy. Cardiac pacing is delivered in response to the absence of sensed intrinsic depolarizations, referred to as P-waves in the atrium and R-waves in the ventricle, upon the expiration of defined escape intervals. Pathologic forms of ventricular tachycardia can often be terminated by anti-tachycardia pacing therapies. Anti-tachycardia pacing therapies are followed by high-energy shock therapy when necessary. Termination of a tachycardia by a shock therapy is commonly referred to as "cardioversion." Ventricular fibrillation (VF) is a form of tachycardia that is a serious life-threatening condition and is normally treated by immediately delivering high-energy shock therapy. Termination of VF is commonly referred to as "defibrillation." Accurate arrhythmia detection and discrimination are important in selecting the appropriate therapy and avoiding the delivery of unnecessary or unsuccessful cardioversion/defibrillation (CV/DF) shocks, which are painful to the patient.

In past practice, ICD systems have employed intra-cardiac electrodes carried by transveous leads for sensing cardiac electrical signals and delivering electrical therapies. Emerging ICD systems are adapted for subcutaneous or submuscular implantation and employ electrodes incorporated on the ICD housing and/or carried by subcutaneous or submuscular leads. These systems, referred to generally herein as "subcutaneous ICD" or "SubQ ICD" systems, do not rely on electrodes implanted in contact with the heart. SubQ ICD systems are less invasive and are therefore implanted more easily and quickly than ICD systems which employ intra-cardiac electrodes. However, greater challenges exist in reliably detecting cardiac arrhythmias using a subcutaneous system. The R-wave amplitude on a SubQ ECG signal may be on the order of one-tenth to one-one hundredth of the amplitude of intra-ventricular sensed R-waves. Furthermore, the signal quality of subcutaneously sensed ECG signals are likely to be more affected by myopotential noise, environmental noise, patient posture and patient activity than EGM signals sensed using intracardiac electrodes. As such, systems and methods that promote reliable and accurate detection of arrhythmias using subcutaneous electrodes are needed.

DETAILED DESCRIPTION

Figure 1:
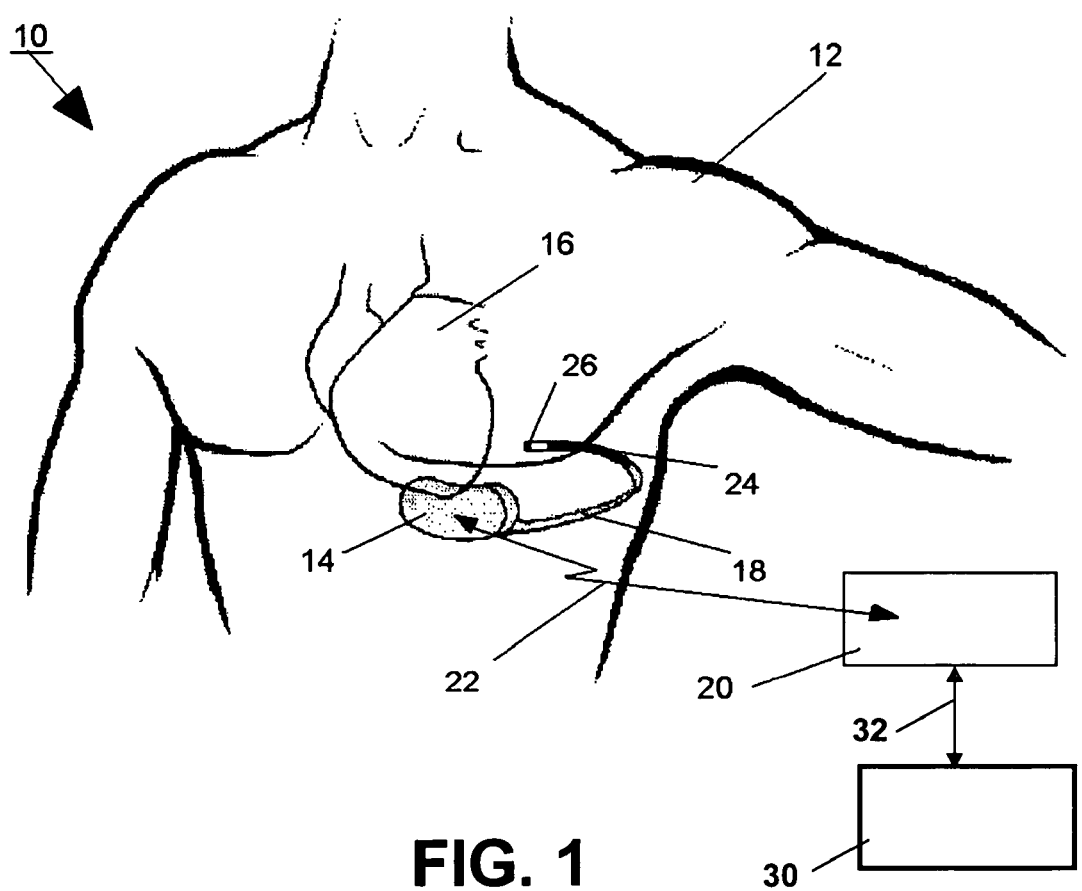
FIG. 1 depicts one example of a SubQ ICD in which the present invention may be embodied.

In the following description, references are made to illustrative embodiments for carrying out the invention. It is understood that other embodiments may be utilized without departing from the scope of the invention. For purposes of clarity, the same reference numbers are used in the drawings to identify similar elements.

The invention is directed toward a subcutaneously implantable medical device system and associated method for monitoring the quality of signals sensed by the implanted device and generating a response when the quality of the signals is below an acceptable level. The term "subcutaneous" as used herein with regard to electrodes and leads generally refers to any electrode or lead that is adapted for implantation in a subcutaneous, submuscular, or any other internal body location that is not in contact with the heart. The sensed signals are generally used by the device for accumulating diagnostic data and/or for detecting the need for delivering a therapy. If the signal quality is below an acceptable level, the usefulness of the signals for diagnostic purposes will be limited. Furthermore, the low quality signals may be unreliable in detecting a need for delivering a therapy, potentially resulting in inappropriately withholding a therapy when a therapy is actually needed or, conversely, delivering an unnecessary therapy. With regard to SubQ ICD systems, the delivery of unneeded therapies unduly exposes the patient to painful shocking pulses. Failure to deliver a needed therapy can result in life-threatening consequences.

FIG. 1 depicts one example of a SubQ ICD 14 in which the present invention may be embodied. SubQ ICD 14 is implanted subcutaneously in a patient 12, outside the ribcage and anterior to the cardiac notch. A subcutaneous lead 18 carrying a sensing electrode 26 and a high-voltage, cardioversion defibrillation coil electrode 24, is electrically coupled at its proximal end to SubQ ICD 14. The distal end of lead 18 is tunneled subcutaneously into a location adjacent to a portion of the latissimus dorsi muscle of patient 12. Specifically, lead 18 is tunneled subcutaneously from the median implant pocket of SubQ ICD 14 laterally and posterially to the patient's back to a location opposite the heart such that the heart 16 is generally disposed between the SubQ ICD 14 and distal electrode coil 24 and distal sensing electrode 26.

An external device 20 is shown in telemetric communication with SubQ ICD 14 by RF communication link 22. External device 20 may be a programmer, home monitor, hand-held or other device adapted to communicate with SubQ ICD 14. Communication link 22 may be any appropriate RF link, including Bluetooth, WiFi, MICS, or as generally described in U.S. Pat. No. 5,683,432 "Adaptive Performance-Optimizing Communication System for Communicating with an Implantable Medical Device" to Goedeke, et al., hereby incorporated herein by reference in its entirety.

External device 20 may be Internet enabled or coupled to a communication network 32 to allow communication between external device 20 and a networked device 30. Networked device 30 may be a Web-based centralized patient management database, a computer, a cell phone or other hand-held device. Networked device 30 communicates with external device 20 via communications network 32, which may be an Internet connection, a local area network, a wide area network, a land line or satellite based telephone network, or cable network. Networked device 30 may be used to remotely monitor and program SubQ ICD 14 via external device 20. Systems and methods for remotely communicating with an implantable medical device are generally disclosed in U.S. Pat. No. 5,752,976 to Duffin et al., U.S. Pat. No. 6,480,745 to Nelson et al., and U.S. Pat. No. 6,418,346 to Nelson et al., and U.S. Pat. No. 6,250,309 to Krichen et al., all of which patents are hereby incorporated herein by reference in their entirety.

Figure 2:
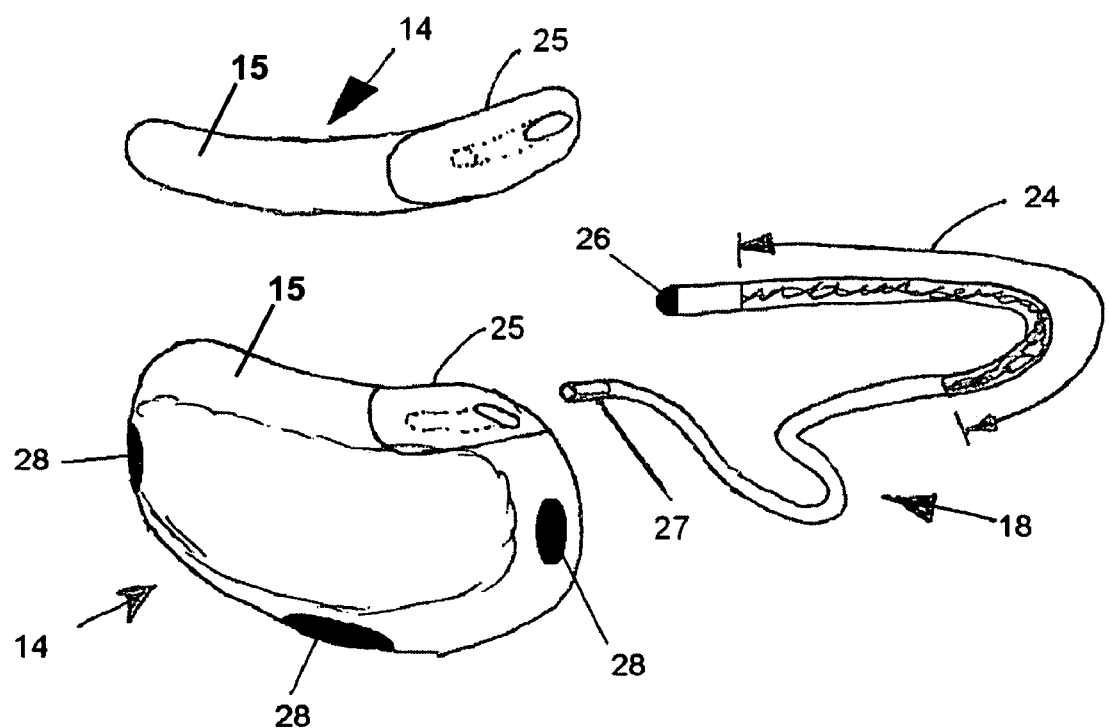
FIG. 2 is a top and plan view of the SubQ ICD shown in FIG. 1.

FIG. 2 is a top and plan view of SubQ ICD 14. SubQ ICD 14 includes a generally ovoid housing 15 having a substantially kidney-shaped profile. Connector block 25 is coupled to housing 15 for receiving the connector assembly 27 of subcutaneous lead 18. SubQ ICD housing 15 may be constructed of stainless steel, titanium or ceramic as described in U.S. Pat. No. 4,180,078 "Lead Connector for a Body Implantable Stimulator" to Anderson and U.S. Pat. No.5,470,345 "Implantable Medical Device with Multi-layered Ceramic Enclosure" to Hassler, et al, both incorporated herein by reference in their entireties. Electronics circuitry enclosed in housing 15 of SubQ ICD 14 may be incorporated on a polyamide flex circuit, printed circuit board (PCB) or ceramic substrate with integrated circuits packaged in leadless chip carriers and/or chip scale packaging (CSP). The plan view shows the generally ovoid construction of housing 15 that promotes ease of subcutaneous implant. This structure is ergonomically adapted to minimize patient discomfort during normal body movement and flexing of the thoracic musculature.

Subcutaneous lead 18 includes distal coil electrode 24, distal sensing electrode 26, an insulated flexible lead body and a proximal connector assembly 27 adapted for connection to SubQ ICD 14 via SubQ ICD connector block 25. Distal sensing electrode 26 is sized appropriately to match the sensing impedance of a housing-based subcutaneous electrode array (SEA) 28. SEA 28 includes a plurality of electrodes mounted on the housing 15. Three electrodes positioned in an orthogonal arrangement are included in SEA 28 in the embodiment shown in FIG. 2. Other embodiments of a SubQ ICD may include any number of electrodes mounted on or incorporated in housing 15. It is recognized that any combination of lead-based and/or housing based electrodes may be used for sensing subcutaneous ECG signals. Multiple subcutaneous electrodes are provided to allow multiple subcutaneous ECG sensing vector configurations.

Electrode assemblies included in SEA 28 are welded into place on the flattened periphery of the housing of SubQ ICD 14. The complete periphery of the SubQ ICD may be manufactured to have a slightly flattened perspective with rounded edges to accommodate the placement of SEA assemblies. The SEA electrode assemblies are welded to SubQ ICD housing 15 (in a manner that preserves hermaticity of the housing 15) and are connected via wires (not shown in FIG. 2) to internal electronic circuitry (described herein below) inside housing 15. SEA electrode assemblies may be constructed of flat plates, or alternatively, spiral electrodes as described in U.S. Pat. No. 6,512,940 "Subcutaneous Spiral Electrode for Sensing Electrical Signals of the Heart" to Brabec, et al. SEA electrode assembly are mounted in a non-conductive surround shroud, for example as generally described in U.S. Pat. No. 6,522,915 "Surround Shroud Connector and Electrode Housings for a Subcutaneous Electrode Array and Leadless ECGs" to Ceballos, et al. or in U.S. Pat. No. 6,622,046 "Subcutaneous Sensing Feedthrough/Electrode Assembly" to Fraley, et al., all of which patents are hereby incorporated herein by reference in their entireties.

Figure 3:
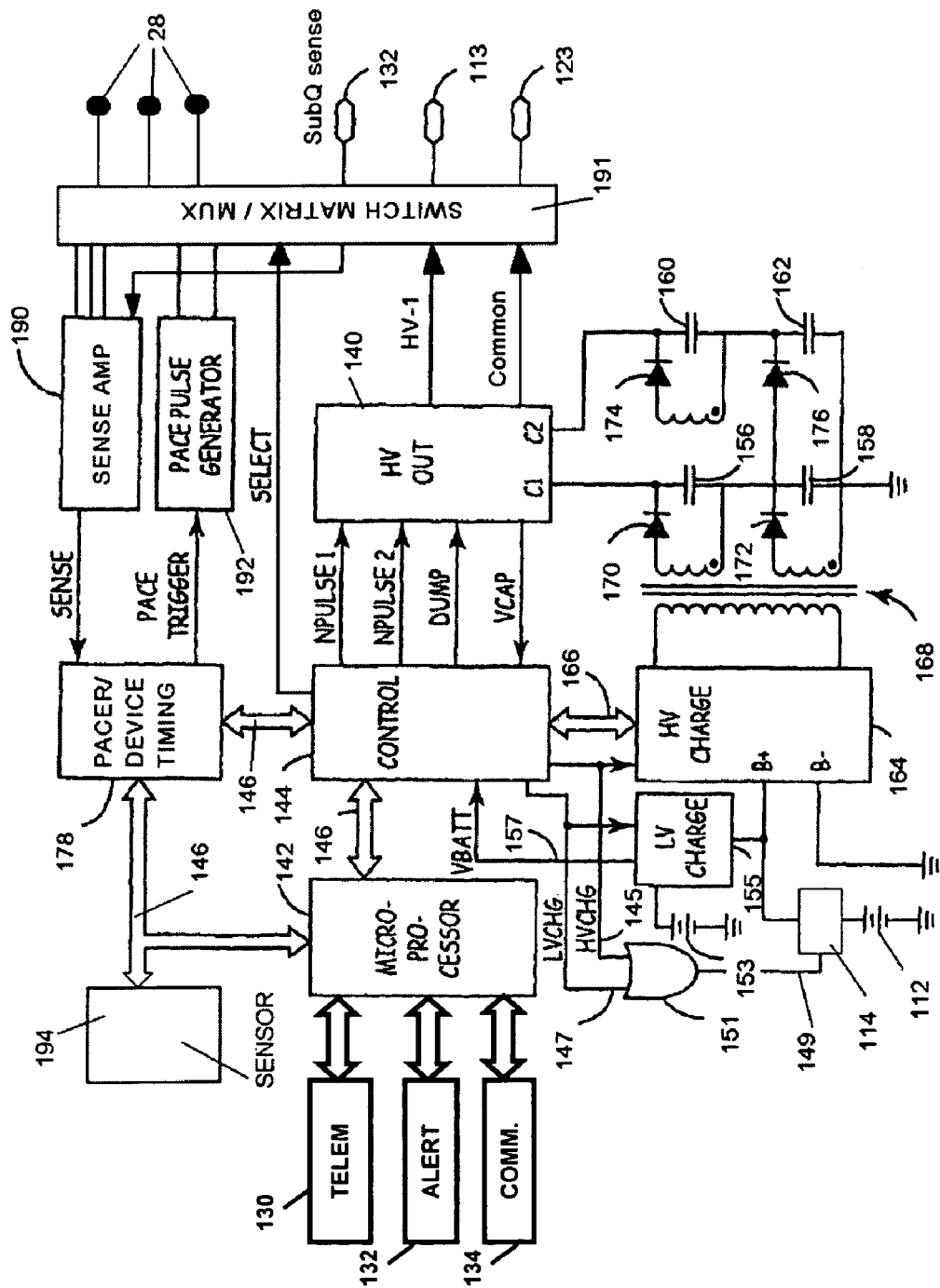
FIG. 3 depicts electronic circuitry enclosed within the hermetically sealed housing of the SubQ ICD.

The electronic circuitry employed in SubQ ICD 14 can take any of the known forms that detect a tachyarrhythmia from the sensed ECG and provide cardioversion/defibrillation shocks as well as post-shock pacing as needed while the heart recovers. A simplified block diagram of such circuitry adapted to function employing subcutaneous sensing and cardioversion/defibrillation electrodes as described herein is shown in FIG. 3. It will be understood by a skilled artisan that the simplified block diagram of FIG. 3 does not show all of the conventional components and circuitry included in an ICD such as digital clocks and clock lines, low voltage power supply and supply lines for powering the circuits and providing pacing pulses.

FIG. 3 depicts the electronic circuitry including low voltage and high voltage batteries enclosed within the hermetically sealed housing of SubQ ICD 14. SubQ ICD 14 functions are controlled by means of software, firmware and hardware that cooperatively monitor the ECG, determine when a CV/DF shock or pacing is necessary, and deliver prescribed CV/DF and pacing therapies. The particular architecture of SubQ ICD 14 for controlling and executing device functions may include application specific integrated circuit (ASIC), an electronic circuit, a processor (shared, dedicated, or group) and memory that execute one or more software or firmware programs, a combinational logic circuit, or other suitable components or combinations of components that provide the described functionality.

Such functionality includes delivering single phase, simultaneous biphasic, or sequential biphasic CV/DF shocks using the SubQ ICD housing 15 (shown in FIG. 2) coupled to the COMMON output 123 of high voltage output circuit 140 and CV/DF electrode 24 (shown in FIG. 1) coupled to the HV output terminal 113. Circuitry for delivering CV/DF shocks may generally correspond to circuitry set forth in commonly assigned U.S. Pat. No. 5,163,427 "Apparatus for Delivering Single and Multiple Cardioversion and Defibrillation Pulses" to Keimel and U.S. Pat. No. 5,188,105 "Apparatus and Method for Treating a Tachyarrhythmia" to Keimel, both of which patents are hereby incorporated herein by reference in their entirety.

The CV/DF shock energy and capacitor charge voltages provided by SubQ ICD 14 are generally intermediate to those supplied by ICDs having at least one CV/DF electrode in contact with the heart and most automatic external defibrillators (AEDs) having CV/DF electrodes in contact with the skin. The typical maximum voltage necessary for ICDs employing an intra-cardiac electrode delivering most biphasic waveforms is approximately 750 Volts with an associated maximum energy of approximately 40 Joules. The typical maximum voltage necessary for defibrillation by AEDs is approximately 2000-5000 Volts with an associated maximum energy of approximately 200-360 Joules depending upon the model and waveform used. A SubQ ICD will use maximum CV/DF voltages in the range of about 700 to about 3150 Volts, associated with energies of about 25 Joules to about 210 Joules. The total high voltage capacitance could range from about 50 to about 300 microfarads. Such CV/DF shocks are only delivered when a malignant tachyarrhythmia, e.g., ventricular fibrillation, is detected through processing of the far field cardiac ECG signals.

In FIG. 3, sense amp 190 in conjunction with pacer/device timing circuit 178 processes the far field ECG sense signals received from sensing vectors selected from SEA 28 (FIG. 2) and sensing electrode 26, or, optionally, a virtual signal created from a combination of the set of physical sensing vectors, if selected. In one embodiment, 2 ECG sensing vectors are selected from the six possible vectors between the three electrodes included in SEA 28 and the lead-based sensing electrode 26. The selection of the sensing electrode pairs are made through the switch matrix/multiplexer 191 in a manner to provide the most reliable R-wave sensing and arrhythmia detection of the ECG signal. The far field ECG signals are passed through the switch matrix/multiplexer 191 to the input of the sense amplifier 190 that, in conjunction with pacer/device timing circuit 178, evaluates the sensed ECG signals. Signal processing methods that may be implemented in sense amplifier 190 and pacer/device timing circuit 178 will be described in greater detail below. Sensing subcutaneous ECG signals in the presence of noise may be aided by the use of appropriate denial and extensible accommodation periods as described in U.S. Pat. No. 6,236,882 "Noise Rejection for Monitoring ECGs" to Lee, et al and incorporated herein by reference in its entirety.

Bradycardia, or asystole, is typically determined by expiration of an escape interval timer within the pacer timing circuit 178 and/or the control circuit 144. Pace trigger signals are applied to the pacing pulse generator 192 causing generation of pacing pulses when the escape interval expires (the interval between successive R-waves exceeds the escape interval). Bradycardia pacing is often temporarily provided to maintain cardiac output during recovery from a CV/DF shock. Pace pulse generator 192 provides pacing pulses that are higher voltage pulses compared to pacing pulses delivered by intracardiac electrodes. Pace pulse generator 192 may be incorporated in the HV output circuitry 140 for delivering pacing pulses of adequate energy for capturing the heart using subcutaneous electrodes.

Detection of a malignant tachyarrhythmia is determined in the control circuit 144 as a function of the intervals between R-wave sense event signals determined from one or more of the selected ECG signals. The R-wave sense event signals are output from the pacer/device timing 178 and sense amplifier circuit 190 to the timing and control circuit 144. It should be noted that implemented arrhythmia detection algorithms may utilize not only interval based signal analysis methods but also supplemental sensors and morphology processing methods and apparatus.

Supplemental sensors such as tissue color, tissue oxygenation, respiration, patient activity and the like may be used to contribute to the decision to apply or withhold a defibrillation therapy as described generally in U.S. Pat. No. 5,464,434 "Medical Interventional Device Responsive to Sudden Hemodynamic Change" to Alt, hereby incorporated herein by reference in its entirety. Sensor processing block 194 provides sensor data to microprocessor 142 via data bus 146. Specifically, patient activity and/or posture may be determined by the apparatus and method as described in U.S. Pat. No. 5,593,431 "Medical Service Employing Multiple DC Accelerometers for Patient Activity and Posture Sensing and Method" to Sheldon, hereby incorporated herein by reference in its entirety. Patient respiration may be determined by the apparatus and method as described in U.S. Pat. No. 4,567,892 "Implantable Cardiac Pacemaker" to Plicchi, et al., hereby incorporated herein by reference in its entirety. Patient tissue oxygenation or tissue color may be determined by the sensor apparatus and method as described in U.S. Pat. No. 5,176,137 to Erickson, et al and incorporated herein by reference in its entirety. The oxygen sensor of the '137 patent may be located in the SubQ ICD pocket or, alternatively, located on the lead 18 to enable the sensing of contacting or near-contacting tissue oxygenation or color.

Certain steps in the performance of the arrhythmia detection algorithm criteria are cooperatively performed in microcomputer 142, including microprocessor, RAM and ROM, associated circuitry, and stored detection criteria that may be programmed into RAM via a telemetry interface 130 conventional in the art. Data and commands are exchanged between microcomputer 142 and timing and control circuit 144, pacer/device timing circuit 178, and high voltage output circuit 140 via a bi-directional data/control bus 146. The pacer/device timing circuit 178 and the control circuit 144 are clocked at a slow clock rate. The microcomputer 142 is normally asleep, but is awakened and operated by a fast clock by interrupts developed by each R-wave sense event, on receipt of a downlink telemetry programming instruction or upon delivery of cardiac pacing pulses to perform any necessary mathematical calculations, to perform tachycardia and fibrillation detection procedures, and to update the time intervals monitored and controlled by the timers in pacer/device timing circuitry 178.

The algorithms and functions of the microcomputer 142 and control circuit 144 employed and performed in detection of tachyarrhythmias are set forth, for example, in commonly assigned U.S. Pat. No. 5,354,316 "Method and Apparatus for Detection and Treatment of Tachycardia and Fibrillation" to Keimel; U.S. Pat. No. 5,545,186 "Prioritized Rule Based Method and Apparatus for Diagnosis and Treatment of Arrhythmias" to Olson, et al., U.S. Pat. No. 5,855,593 "Prioritized Rule Based Method and Apparatus for Diagnosis and Treatment of Arrhythmias" to Olson, et al.; and U.S. Pat. No. 5,193,535 "Method and Apparatus for Discrimination of Ventricular Tachycardia from Ventricular Fibrillation and Treatment Thereof" to Bardy, et al., all of which patents are hereby incorporated herein by reference in their entireties. Particular algorithms for detection of ventricular fibrillation and malignant ventricular tachycardias can be selected from among the comprehensive algorithms for distinguishing atrial and ventricular tachyarrhythmias from one another and from high rate sinus rhythms as set forth, for example, in the '316, '186, '593 and '593 patents.

The detection algorithms are highly sensitive and specific for the presence or absence of life threatening ventricular arrhythmias, e.g., ventricular tachycardia (VT) and ventricular fibrillation (VF). Operational circuitry may detect the presence of atrial fibrillation (A FIB). A-FIB detection can include using R—R cycle length instability detection algorithms, for example as generally disclosed in U.S. Pat. Publication No. 2004/0092836 (Ritscher et al.). If A-FIB has been detected, the operational circuitry may provide QRS synchronized atrial CV/DF using a similar range of shock energy and wave shapes used for ventricular CV/DF.

Operating modes and parameters of the detection algorithm are programmable. The detection algorithm is particularly focused on the detection of VF and high rate VT (for example rates greater than 170 bpm). As part of the detection algorithm's applicability to children, the upper rate range is programmable upward for use in children, known to have rapid supraventricular tachycardias and more rapid VF.

When a malignant tachycardia is detected, high voltage capacitors 156, 158, 160, and 162 are charged to a pre-programmed voltage level by a high-voltage charging circuit 164. It is generally considered inefficient to maintain a constant charge on the high voltage output capacitors 156, 158, 160, 162. Instead, charging is initiated when control circuit 144 issues a high voltage charge command HVCHG delivered on line 145 to high voltage charge circuit 164 and charging is controlled by means of bi-directional control/data bus 166 and a feedback signal VCAP from the HV output circuit 140. High voltage output capacitors 156, 158, 160 and 162 typically correspond to flat, aluminum electrolytic or wet tantalum construction.

The negative terminal of high voltage battery 112 is directly coupled to system ground. Switch circuit 114 is normally open so that the positive terminal of high voltage battery 112 is disconnected from the positive power input of the high voltage charge circuit 164. The high voltage charge command HVCHG is also conducted via conductor 149 to the control input of switch circuit 114, and switch circuit 114 closes in response to connect positive high voltage battery voltage EXT B+ to the positive power input of high voltage charge circuit 164. Switch circuit 114 may be, for example, a field effect transistor (FET) with its source-to-drain path interrupting the EXT B+ conductor 118 and its gate receiving the HVCHG signal on conductor 145. High voltage charge circuit 164 is thereby rendered ready to begin charging the high voltage output capacitors 156, 158, 160, and 162 with charging current from high voltage battery 112.

High voltage output capacitors 156, 158, 160, and 162 may be charged to very high voltages, e.g., 700-3150V, to be discharged through the body and heart between the subcutaneous electrode coupled to HV output terminal 113 and COMMON 123. High voltage capacitors 156, 158, 160 and 162 are charged by high voltage charge circuit 164 and a high frequency, high-voltage transformer 168, for example as set forth in commonly assigned U.S. Pat. No. 4,548,209 "Energy Converter for Implantable Cardioverter" to Wielders, et al. Proper charging polarities are maintained by diodes 170, 172, 174 and 176 interconnecting the output windings of high-voltage transformer 168 and the capacitors 156, 158, 160, and 162. As noted above, the state of capacitor charge is monitored by circuitry within the high voltage output circuit 140 that provides a VCAP, feedback signal indicative of the voltage to the timing and control circuit 144. Timing and control circuit 144 terminates the high voltage charge command HVCHG when the VCAP signal matches the programmed capacitor output voltage, i.e., the CV/DF peak shock voltage.

Control circuit 144 then develops first and second control signals NPULSE 1 and NPULSE 2, respectively, that are applied to the high voltage output circuit 140 for triggering the delivery of cardioverting or defibrillating shocks. In particular, the NPULSE 1 signal triggers discharge of the first capacitor bank, comprising capacitors 156 and 158. The NPULSE 2 signal triggers discharge of the first capacitor bank and a second capacitor bank, comprising capacitors 160 and 162. It is possible to select between a plurality of output pulse regimes simply by modifying the number and time order of assertion of the NPULSE 1 and NPULSE 2 signals. The NPULSE 1 signals and NPULSE 2 signals may be provided sequentially, simultaneously or individually. In this way, control circuitry 144 serves to control operation of the high voltage output stage 140, which delivers high energy CV/DF shocks between the pair of the CV/DF electrodes coupled to the HV-1 terminal 113 and COMMON terminal 123 as shown in FIG. 3.

Thus, SubQ ICD 14 monitors the patient's cardiac status and initiates the delivery of a CV/DF shock through the CV/DF electrodes coupled to terminals 113 and 123 in response to detection of a tachyarrhythmia requiring CV/DF. The high HVCHG signal causes the high voltage battery 112 to be connected through the switch circuit 114 with the high voltage charge circuit 164 and the charging of output capacitors 156, 158, 160, and 162 to commence. Charging continues until the programmed charge voltage is reflected by the VCAP signal, at which point control and timing circuit 144 sets the HVCHG signal low terminating charging and opening switch circuit 114. Typically, the charging cycle takes only fifteen to twenty seconds, and occurs very infrequently. The SubQ ICD 14 can be programmed to attempt to deliver cardioversion shocks to the heart in the manners described above in timed synchrony with a detected R-wave or can be programmed or fabricated to deliver defibrillation shocks to the heart in the manners described above without attempting to synchronize the delivery to a detected R-wave. Episode data related to the detection of the tachyarrhythmia and delivery of the CV/DF shock can be stored in RAM for uplink telemetry transmission to an external programmer as is well known in the art to facilitate in diagnosis of the patient's cardiac state. A patient receiving SubQ ICD 14 on a prophylactic basis would be instructed to report each such episode to the attending physician for further evaluation of the patient's condition and assessment for the need for implantation of a more sophisticated and long-lived ICD.

SubQ ICD 14 includes telemetry circuit 130 so that it is capable of being programmed by means of external programmer via a bidirectional telemetry link 22 (shown in FIG. 1). Uplink telemetry allows device status and diagnostic/event data to be sent to an external device 20 for review by the patient's physician. Downlink telemetry allows the external programmer via physician control to allow the programming of device function and the optimization of the detection and therapy for a specific patient.

Programmers and telemetry systems suitable for use in the practice of the present invention have been well known for many years. Known programmers typically communicate with an implanted device via a bi-directional radio-frequency telemetry link, so that the programmer can transmit control commands and operational parameter values to be received by the implanted device, and so that the implanted device can communicate diagnostic and operational data to the programmer. Programmers believed to be suitable for the purposes of practicing the present invention include the Models 9790 and Care Link® programmers, commercially available from Medtronic, Inc., Minneapolis, Minn. Various telemetry systems for providing the necessary communications channels between an external programming unit and an implanted device have been developed and are well known in the art. Telemetry systems believed to be suitable for the purposes of practicing the present invention are disclosed, for example, in the following U.S. patents: U.S. Pat. No. 5,127,404 to Wyborny et al. entitled "Telemetry Format for Implanted Medical Device"; U.S. Pat. No. 4,374,382 to Markowitz entitled "Marker Channel Telemetry System for a Medical Device"; and U.S. Pat. No. 4,556,063 to Thompson et al. entitled "Telemetry System for a Medical Device". The Wyborny et al. '404, Markowitz '382, and Thompson et al. '063 patents are commonly assigned to the assignee of the present invention, and are each hereby incorporated by reference herein in their respective entireties. SubQ ICD 14 may employ a distance telemetry system that does not require the use of a programming head, for example, as generally disclosed in U.S. Pat. No. 6,482,154 to Haubrich et al., hereby incorporated herein by reference in its entirety.

SubQ ICD 14 may further include patient alert circuitry 132. Patient alert circuitry 132 delivers a sensory signal perceivable by the patient for notifying the patient of particular events or conditions detected by SubQ ICD 14. In accordance with one embodiment of the invention, patient alert circuitry 132 generates an alert signal when the signal quality of selected subcutaneous ECG sensing vectors falls below an alert level. Patient alert circuitry 132 may be provided for broadcasting sounds audible by the patient, delivering stimulation pulses to the thoracic musculature in the region of SubQ ICD 14 or lead 18 using any available electrodes, or causing SubQ ICD 14 to vibrate. Patient alert circuitry may correspond to the audible patient alert generally disclosed in U.S. Pat. No. 6,450,172 to Hartlaub et al., hereby incorporated herein by reference in its entirety.

SubQ ICD 14 may further include a communications unit 134 for allowing wireless communication directly between SubQ ICD 14 and a wireless communication networked device 30 (shown in FIG. 1), such as a cell phone, hand-held device, or computer using WiFi, Bluetooth, or other wireless RF connection.

Figure 4:
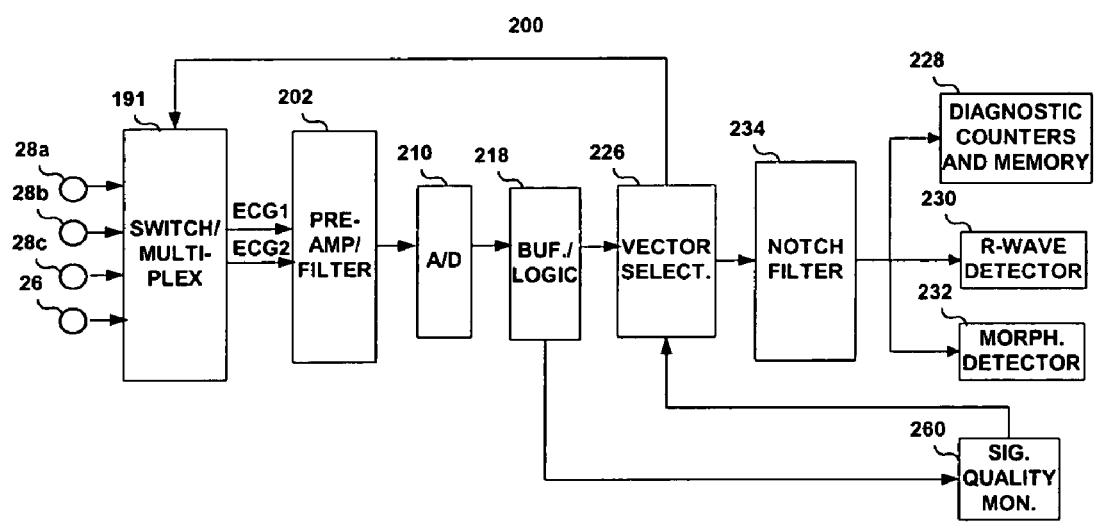
FIG. 4 shows a block diagram summarizing signal processing methods performed by the SubQ ICD.

FIG. 4 shows a block diagram 200 summarizing signal processing methods performed by the SubQ ICD 14. Subcutaneous ECG signals sensed between sensing vectors defined by each paired combination of the three electrodes included in SEA 28 and the lead based sensing electrode 26 are selected through switch/multiplexer 191. In the embodiment shown, two ECG signals, ECG1 and ECG2, out of six possible ECG signals are selected from SEA 28 and sensing electrode 26 by switch/multiplexer 191. The selected signals are amplified and bandpass filtered (e.g. 2.5-105 Hz) by preamplifier 202. Pre-amplifier 202 is included in sense amplifier circuitry 190 (shown in FIG. 3).

The amplified and filtered signals are directed to A/D converter 210 which operates to sample the time varying analog ECG signals to provide a digitized ECG signal to temporary buffers/control logic 218. Temporary buffers/control logic 218 shifts the digital data through stages in a FIFO manner under the control of pacer/device timing circuit 178 (FIG. 3). Vector selection block 226 operates to identify the two out of six ECG sensing vectors having optimal signal quality for sensing cardiac signals. In the embodiment shown, the six possible ECG sensing vectors are selected two at a time by switch/multiplexer 191 for evaluation by vector selection block 226. It is recognized that in alternative embodiments one or more ECG sensing vectors may be selected simultaneously or sequentially for evaluation by vector selection block 226 and for signal quality monitoring as will be described below.

Vector selection may include methods generally disclosed in U.S. Pat. No. 5,331,966 "Subcutaneous Multi-Electrode Sensing System, Method and Pacer" to Bennett, et al. In some embodiments, vector selection block 226 may generate a virtual vector signal as some combination of the physical vectors under control of microprocessor 142 and control block 144 (FIG. 3) as generally described in U.S. Pat. No. 6,505,067 "System and Method for Deriving Virtual ECG or EGM Signal" to Lee, et al. Both patents are hereby incorporated herein by reference in their entireties. ECG sensing vector selection may be determined by the patient's physician and programmed via telemetry link 22 from external device 20 or, alternatively, may be automatically selected by SubQ ICD 14 under control of microprocessor 142 (FIG. 3) by selecting the vector(s) having the greatest signal quality or signal independence (uniqueness).

In order to automatically select the ECG sensing vectors, the ECG signal quality is evaluated by determining a vector selection metric for each sensing vector. "Quality" is defined as the signal's ability to provide accurate heart rate estimation and accurate morphological waveform separation between the patient's usual sinus rhythm and the patient's ventricular tachyarrhythmia. Determining a vector selection metric may include determining a signal amplitude such as an R-wave amplitude, a signal-to-noise ratio such as an R-wave peak amplitude to a maximum or average waveform amplitude between R-waves or an R-wave to T-wave amplitude ratio, a signal slope or slew rate, a low slope content, a relative high versus low frequency power, mean frequency or spectral width estimation, probability density function, normalized mean rectified amplitude, or any combination of these metrics or other signal quality estimation.

Automatic vector selection might be done at implantation, periodically (daily, weekly, monthly) or both. At implant, automatic vector selection may be initiated as part of an automatic device turn-on procedure that performs such activities as measuring lead impedances and battery voltages. The device turn-on procedure may be initiated by the implanting physician (e.g., by pressing a programmer button) or, alternatively, may be initiated automatically upon automatic detection of device/lead implantation. The turn-on procedure may also use the automatic vector selection criteria to determine if ECG signal quality is adequate for the current patient and for the device and lead position, prior to suturing SubQ ICD 14 in place and closing the subcutaneous pocket incision. Knowledge of an ECG vector selection metric would allow the implanting physician to maneuver the device and/or lead to a new location or orientation to improve the quality of the ECG signals as required. The preferred vectors might be those vectors with the indices that maximize rate estimation and detection accuracy. There may also be an a priori set of vectors that are preferred by the physician, and as long as those vectors exceed some minimum threshold, or are only slightly worse than some other less desirable vectors, the a priori preferred vectors are chosen. Certain vectors may be considered nearly identical such that they are not tested unless the a priori selected vector index falls below some predetermined threshold.

Depending upon power consumption and power requirements of the device, the vector selection metric may be measured for all available vectors (or alternatively, a subset) as often as desired. Data may be gathered, for example, on a minute, hourly, daily, weekly or monthly basis. More frequent measurements (e.g., every minute) may be averaged over time and used to select vectors based upon susceptibility of vectors to occasional noise, motion noise, or EMI, for example.

Alternatively, the SubQ ICD 14 may have an indicator/sensor of patient activity (piezo-resistive, accelerometer, impedance, or the like) and delay automatic vector measurement during periods of moderate or high patient activity to periods of minimal to no activity. One representative scenario may include testing/evaluating ECG vectors once daily or weekly while the patient has been determined to be asleep, e.g., using an internal clock (e.g., 2:00 am) or, alternatively, infer sleep by determining the patient's position (via a 2- or 3-axis accelerometer) and a lack of activity.

If infrequent automatic, periodic measurements are made, it may also be desirable to measure noise (e.g., muscle, motion, EMI, etc.) in the signal and postpone the vector selection measurement until after the noise has subsided.

SubQ ICD 14 may optionally have an indicator of the patient's posture (via a 2- or 3-axis accelerometer). This sensor may be used to ensure that the differences in ECG quality are not simply a result of changing posture/position. The sensor may be used to gather data in a number of postures so that ECG quality may be averaged over these postures or, alternatively, selected for a preferred posture. For example, there might be a learning period to identify the preferred vectors for a given posture which would be selected when the patient assumes that posture.

In one embodiment, vector selection metric calculations are performed a number of times over approximately 1 minute, once per day, for each vector. These values would be averaged for each vector over the course of one week. Averaging may consist of a moving average or recursive average depending on time weighting and memory considerations. In this example, the sensing vector selection would be performed once per week.

Continuing with FIG. 4, a diagnostic channel 228 receives the selected subcutaneous ECG signals, compresses the digital data, and stores the data in memory or provides the data for uplink telemetry for review by a clinician. The stored data is available for diagnostic functions such as storing detected arrhythmia episodes, or providing data for various event counters or other diagnostic features used to monitor the patient and/or evaluate device function such as an asystole counter, a bradycardia counter, and a minimum sensing threshold counter.

The selected ECG signals are additionally used to provide R-wave interval sensing via R-wave detection block 230. R-wave detection block 230 may include additional filtering of the selected ECG signals and includes a rectifier and auto-threshold block for performing R-wave event detection. Reference is made, for example, to U.S. Pat. No. 5,117,824 "Apparatus for Monitoring Electrical Physiologic Signals" to Keimel, et al; U.S. Publication No. 2004/0049120, "Method and Apparatus for Cardiac R-wave Sensing in a Subcutaneous ECG Waveform" to Cao, et al., and U.S. Publication No. 2004/0260350 "Automatic EGM Amplitude Measurements During Tachyarrhythmia Episodes" to Brandstetter, et al, all incorporated herein by reference in their entireties. R-wave detector 230 performs full wave rectification on the amplified, narrowband ECG signals. A programmable fixed threshold (percentage of peak value), a moving average or, more preferably, an auto-adjusting threshold is generated as described in the '824 patent or '350 publication. Following a detected depolarization, the amplifier is automatically adjusted so that the effective sensing threshold is set to be equal to a predetermined portion of the amplitude of the sensed depolarization, and the effective sensing threshold decays thereafter to a lower or base-sensing threshold. R-wave detector 230 includes a comparator for determining signal crossings from the rectified waveform and auto-adjusted threshold signal. The time interval between consecutive R-waves is determined for subsequent arrhythmia detection. The heart rate estimation may be determined from a predetermined number of consecutive R-R intervals, for example by determining a running mean, median, or minimum interval or other estimation determined from the most recently sensed intervals. The oldest heart rate estimation value is removed as a new data value is added.

The selected ECG signals may be applied to ECG morphology detector 232. Morphology detector 232 may include additional filtering and performs signal morphology evaluation that may be used for subsequent rhythm detection/determination. Morphology evaluation generally includes evaluating predetermined signal characteristics and may include comparing signal complexes obtained from the selected ECG signals to one or more morphology templates previously created and stored for known cardiac rhythms. Morphology template comparisons may include comparisons of one or more waveform features of the sensed ECG signals and the stored template feature. Morphology evaluation may alternatively include performing a wavelet transform to convert the waveform to signal wavelet coefficients which are compared to a corresponding set of template wavelet coefficients derived from known heart rhythms. Examples of signal morphology evaluation methods applied to cardiac signals are generally disclosed in U.S. Pat. No. 6,393,316 (Gillberg, et al.) and U.S. Pat. No. 4,552,154 (Hartlaub, et al.), both of which patents are hereby incorporated herein by reference in their entirety. While particular signal processing blocks are shown in FIG. 4, it is recognized that alternative signal processing circuitry and methods may be implemented for sensing subcutaneous ECG signals and processing sensed signals for use in detecting cardiac arrhythmias.

The signal quality of the selected sensing vectors is monitored at signal quality monitoring block 260 to ensure that the selected ECG sensing vector signal quality remains acceptable for diagnostic or arrhythmia detection purposes. Signal quality monitoring block 260 may receive the currently selected ECG signals from temporary buffer/logic circuitry 218 for monitoring signal quality. Alternatively, all available sensing vector signals may be selected two at a time by switch/multiplexer 191 and provided as input to signal quality monitoring block 260 from temporary buffer/logic 218. Signal quality monitoring block 260 determines a signal quality metric for each sensing vector signal received, as will be described in greater detail below, and compares the metric to a threshold for determining if the sensing vector meets acceptable signal quality criteria. Signal quality monitoring block 260 may provide feedback to vector selection block 226 for triggering selection of a new sensing vector when the signal quality for a currently selected sensing vector is determined to be low. Vector selection block 226 provides feedback used for selecting which two ECG sensing vectors out of the six possible vectors are to be selected by switch/multiplexer 191.

Figure 5:
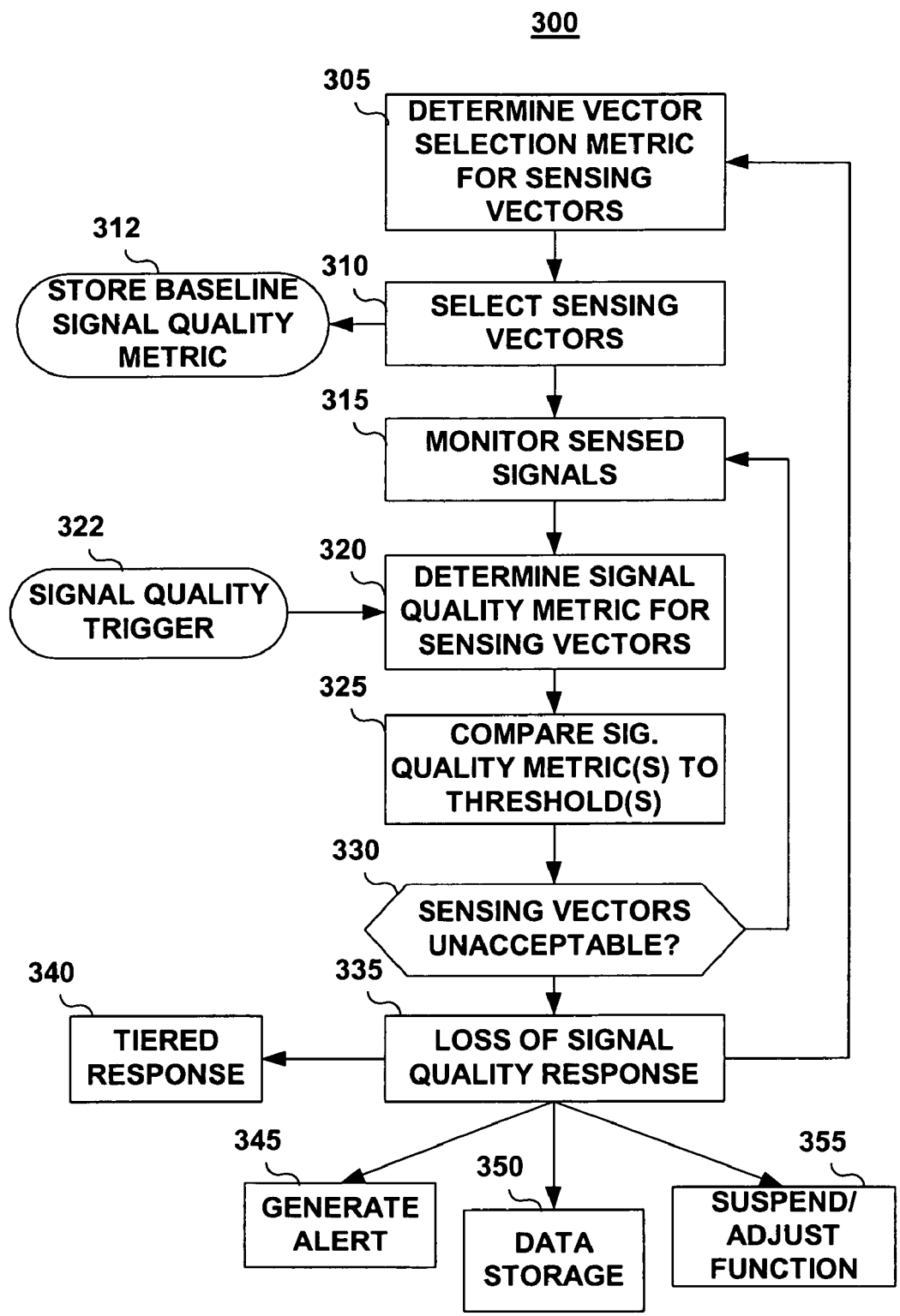
FIG. 5 is a flow chart summarizing steps included in a method for determining subcutaneous sensing vector signal quality and responding to a loss in signal quality.

FIG. 5 is a flow chart summarizing steps included in a method for determining subcutaneous sensing vector signal quality and responding to a loss in signal quality. Flow chart 300 is intended to illustrate the functional operation of the device, and should not be construed as reflective of a specific form of software or hardware necessary to practice the invention. It is believed that the particular form of software will be determined primarily by the particular system architecture employed in the device and by the particular detection and therapy delivery methodologies employed by the device. Providing software to accomplish the present invention in the context of any modern ICD, given the disclosure herein, is within the abilities of one of skill in the art.

At block 305, a vector selection metric is determined for the available subcutaneous sensing vectors. As described above, the vector selection metric may be determined first for one or more preferred sensing vectors and the sensing vectors may be selected based on the determined metric. If the metric does not meet a vector selection threshold, the vector selection metric may be determined for other available sensing vectors. The subcutaneous sensing vector(s) are selected, either automatically or manually, based on the vector selection metrics at step 310.

At block 315, the subcutaneously sensed signals are monitored using the selected sensing vectors according to a programmed operating mode for diagnosing arrhythmias, determining a need for therapy, or storing data for monitoring and diagnostic purposes.

At block 320, a signal quality metric is determined for at least one or all of the selected sensing vectors. The signal quality metric is used to monitor the quality of selected ECG sensing vectors. Accordingly, the signal quality metric will generally be determined more frequently than a vector selection metric; although circumstances may exist in which vector selection occurs more frequently than signal quality monitoring during a limited time period. The signal quality metric for each selected sensing vector is determined on a periodic basis, such as each minute, hourly, or daily. In some embodiments, a signal quality metric that requires minimal processing time and power is monitored on a continuous basis. The signal quality metric may additionally or alternatively be determined in response to triggering events, as indicated by block 322. A triggering event or condition that would cause determination of signal quality metrics may include detecting a high frequency of detected arrhythmias, a high frequency of delivered therapies, or other diagnostic parameters that indicate undersensing or oversensing. Other diagnostic parameters may include an asystole count, a bradycardia count, a short interval count, a sensing at minimum threshold count, or a change in inter-electrode impedance.

The signal quality metric may be defined to be the same or different than the vector selection metric. Determination of the signal quality metric includes calculation of one or more predetermined signal features. Signal features determined may include: a signal amplitude, such as an R-wave amplitude; a signal-to-noise ratio such as an R-wave peak amplitude to a waveform amplitude between R-waves which may be a peak, mean or median amplitude or an R-wave to T-wave amplitude ratio; a signal slope or slew rate such as the slope of the R-wave; a low slope content; a relative high versus low frequency power; mean frequency or spectral width estimation; probability density function; normalized mean rectified amplitude, frequency of sensing at minimum threshold, short interval counter frequency, correlation between cross-channel sense markers, within channel consistency measures, an inter-electrode impedance measurement, or any combination of these metrics or other signal quality estimation, including other examples listed previously.

In some embodiments, a vector selection metric may be more computationally complex than the signal quality metric, requiring greater processing time and power for selecting the most reliable sensing vector. The signal quality metric may be defined such that its computation uses less processing time and power, allowing the signal quality metric to be determined on a more frequent basis. A baseline signal quality metric may be stored at the time of vector selection as indicated by block 312. The baseline signal quality metric may be used during signal quality monitoring to determine if signal quality has deteriorated.

At step 325, the computed signal quality metrics are compared to a threshold. Unique thresholds may be defined for each sensing vector. In some embodiments, the threshold is defined as a function of the stored baseline signal quality metric (block 312), for example a percentage of the baseline signal quality metric. The threshold comparison performed at block 325 may include comparing each signal quality metric to two or more threshold levels to allow different levels of responses to a change in signal quality. Deteriorating signal quality or a loss of signal quality is detected if the signal quality metric crosses a defined threshold. The signal quality threshold may be the same or different than thresholds used for vector selection.

The signal quality metric may be determined for each of the sensing vectors available or may be determined for only the selected sensing vectors. If any of the selected sensing vectors are determined to have a deteriorating or unacceptable ECG signal quality, as determined at step 330 (based on the threshold comparison performed at block 325), a loss of signal quality response is provided at step 335. If the signal quality of each selected sensing vector monitored remains acceptable or unchanged, the SubQ ICD 14 continues monitoring the subcutaneous ECG signals using the selected sensing vectors at block 315. It is recognized that if the signal quality of any of the non-selected sensing vectors is determined to be better than any of the selected sensing vectors, the selected sensing vectors may be changed to ensure that the vectors providing the greatest signal quality are selected.

The loss of signal quality response provided at step 335 includes one or more operations generally aimed at restoring an acceptable signal quality, promoting safe device operation when the subcutaneously sensed ECG signal quality is deemed unacceptable or deteriorated, and/or notifying the patient or a clinician of the loss of signal quality. The loss of signal quality response may be provided when the signal quality metric for one or more of the selected sensing vectors crosses a predetermined threshold. The loss of signal quality response may be based on the number of sensing vectors and/or specifically which sensing vectors (for example an SEA sensing vector or a transthoracic sensing vector) are deemed unacceptable or deteriorating. One response provided at block 335 includes returning to block 305 to perform automatic vector selection as described previously wherein new sensing vectors are selected based on newly determined vector selection metrics and vector selection criteria.

The loss of signal quality response may include generating an alert at block 345, which may be a patient alert and/or a clinician alert. In one embodiment, an alert is generated when the required number of ECG sensing vectors does not meet acceptable signal quality criteria. A patient alert may be generated by an alert circuitry 132 (FIG. 3) included in SubQ ICD 14 which broadcasts audible sounds, vibrates, or delivers stimulation to the thoracic musculature in the vicinity of SubQ ICD 14 or lead 18. A patient alert may alternatively be provided as a visual alert displayed on external device 20 (FIG. 1). The loss of signal quality response at block 335 would cause a signal to be transmitted to the external device 20 which in turn causes device 20 to display a message notifying the patient of a loss of signal quality. A loss of signal quality signal transmitted to external device 20 may be further transmitted along communication network 32 to networked device 30 (shown in FIG. 1) to alert the patient, for example via a cell phone text or voice message or an e-mail message sent via the Internet. A clinician alert may additionally or alternatively be provided by transmitting a signal directly from SubQ ICD 14 using communication module 134 to a communication network or via external device 20 to communication network 32. The loss of signal quality alert may be sent via the communication network 32 to a networked device 30, including a centralized patient management database, a clinician's cell phone or networked computer, or a clinic networked computer.

The loss of signal quality response provided at block 335 may include altering the device operating mode. For example, the SubQ ICD 14 may store sensed ECG data for review by a clinician as indicated at block 350. Certain device functions may be adjusted or suspended at block 355. For example, arrhythmia detection functions may be suspended or detection criteria may be adjusted, for example by requiring a greater number of event intervals to detect or adding detection criteria such as ECG morphological criteria or other criteria sensed from other sensors. Arrhythmia therapy functions may be suspended or adjusted. For example, all therapies may be turned off or only life-saving ventricular defibrillation therapies may remain on.

The loss of signal quality response may include a tiered response as indicated at block 340. A tiered response includes different levels of responses based on the threshold level that is crossed. For example, if the signal quality metric is defined as an R-wave amplitude, two R-wave amplitude threshold levels may be defined. If the R-wave amplitude falls below a first threshold, a low-level loss of signal quality response is provided. A low-level response may be to perform signal quality monitoring at more frequent intervals, perform automatic vector selection to select a new vector, or to deliver a patient alert signal to notify the patient that a change in signal quality has been detected. The patient has been previously instructed to contact his or her clinician for follow-up upon receiving a patient alert signal. If the R-wave amplitude falls below a second, lower threshold, a higher level response is provided, particularly when no acceptable sensing vectors are identified by the automatic vector selection process. The higher level loss of signal quality response may include another patient alert, a clinician alert, or suspending or altering a device function, such as turning arrhythmia therapies off.

In another embodiment, a tiered response may be based on the number of vectors determined to have low signal quality. A low-level signal quality response may be provided when at least one sensing vector does not meet the signal quality threshold. The low-level response may include performing automatic vector selection. A higher level response may be provided when the required number of ECG sensing vectors does not meet the signal quality threshold requirement. The higher level response may include generating an alarm.

It is understood that the signal quality metric, the thresholds used to evaluate the signal quality metric for determining a loss of signal quality, and the loss of signal quality responses may be defined according to programmable parameters that are selected based on clinician preference or tailored based on individual patient need. The signal quality metric, the thresholds, and the responses may each include a combination of metrics, thresholds and responses, respectively, for detecting a loss in signal quality and responding appropriately thereto. Furthermore, the clinician may have the option to disable vector selection and/or signal quality monitoring to prevent changes in selected sensing vectors.

Thus, an implantable medical device system and associated method for monitoring the quality of subcutaneously sensed ECG signals have been presented in the foregoing description with reference to specific embodiments. It is appreciated that various modifications to the referenced embodiments may be made without departing from the scope of the invention as set forth in the following claims.

The invention claimed is:

1. An implantable medical device system, comprising:
   a plurality of subcutaneous electrodes forming a plurality of subcutaneous sensing vectors;
   a sensing circuit for receiving signals from the plurality of subcutaneous sensing vectors;
   a processor for determining a first signal quality metric in response to a first subcutaneous sensing vector signal, comparing the first signal quality metric to a predetermined threshold, and generating a first loss of signal quality response in response to the first signal quality metric crossing the threshold
   wherein determining the first signal quality metric comprises calculation of a characteristic of the vector signal, the characteristic corresponding to the quality of the vector signal for providing accurate separation of a sinus rhythm of a patient and a tachyarrhythmia of the patient.

2. The system of claim 1 wherein the processor further determines a second signal quality metric for a second subcutaneous sensing vector signal, compares the second signal quality metric to the predetermined threshold, and generates a second loss of signal quality response in response to both the first and the second signal quality metric crossing the threshold.

3. The system of claim 2 wherein the predetermined threshold includes a first threshold applied to the first signal quality metric and a second threshold applied to the second signal quality metric.

4. The system of claim 1 wherein the first loss of signal quality response includes any of: generating an alert signal, selecting a different sensing vector, suspending a device function, adjusting a device function, and increasing the frequency of determining the first signal quality metric.

5. The system of claim 4 further including an implantable medical device telemetry circuit and an external device adapted for bidirectional communication with the telemetry circuit and wherein generating the alert signal includes transmitting a signal between the implantable medical device telemetry circuit and the external device.

6. The system of claim 4 further including an alert module and wherein generating the alert signal includes generating a sensory stimulus perceivable by the patient.

7. The system of claim 1 further including a communications module adapted for communicating with a communications network and wherein the first loss of signal quality response includes transferring a signal to the communications network.

8. The system of claim 1 wherein the plurality of subcutaneous electrodes includes electrodes carried by a subcutaneous lead.

9. The system of claim 1 wherein the received signals include cardiac electrogram signals.

10. The system of claim 1 wherein the determining the signal quality includes determining any of a signal amplitude, a signal-to-noise ratio, a total signal energy, a signal slope, a signal frequency, a frequency of sensing at a minimum sensing threshold, a frequency of short intervals, a cross-correlation metric, a channel consistency metric, and an inter-electrode impedance.

11. The system of claim 1 wherein the processor further compares the first signal quality metric to a low-level response threshold and generates a low-level loss of signal quality response in response to the signal quality metric crossing the low-level response threshold.

12. The system of claim 1 wherein the processor further determines a vector selection metric for each of the plurality of sensing vectors, and selects one or more sensing vectors based on a comparison of the vector selection metric to a vector selection threshold.

13. A method for use in a subcutaneously implanted medical device system, comprising:
   selecting a plurality of subcutaneous sensing vectors from a plurality of subcutaneous electrodes;
   sensing signals from the selected plurality of subcutaneous sensing vectors;
   determining a first signal quality metric in response to a first selected subcutaneous sensing vector signal, comparing the first signal quality metric to a predetermined threshold, and generating a first loss of signal quality response in response to the first signal quality metric crossing the threshold
   wherein determining the first signal quality metric comprises calculation of a characteristic of the vector signal, the characteristic corresponding to the quality of the vector signal for providing accurate separation of a sinus rhythm of a patient and an arrhythmia of the patient.

14. The method of claim 13 further comprising determining a second signal quality metric for a second selected subcutaneous sensing vector signal, comparing the second signal quality metric to the predetermined threshold, and generating a second loss of signal quality response in response to both the first and the second signal quality metric crossing the threshold.

15. The method of claim 14 wherein the predetermined threshold includes a first threshold applied to the first signal quality metric and a second threshold applied to the second signal quality metric.

16. The method of claim 13 wherein the first loss of signal quality response includes any of: generating an alert signal, selecting a different sensing vector, suspending a device function, adjusting a device function, and increasing the frequency of determining the first signal quality metric.

17. The method of claim 16 further wherein generating the alert signal includes transmitting a signal between an implantable medical device telemetry circuit and an external device.

18. The method of claim 16 wherein the alert signal includes generating a generating a sensory stimulus perceivable by the patient.

19. The method of claim 13 wherein the first loss of signal quality response includes transferring an alert signal to a communications network.

20. The method of claim 13 wherein the plurality of subcutaneous electrodes includes electrodes carried by a subcutaneous lead.

21. The method of claim 13 wherein the sensed signals include cardiac electrogram signals.

22. The method of claim 13 wherein determining the signal quality metric includes determining any of a signal amplitude, signal-to-noise ratio, a total signal energy, a signal slope, and a low slope content.

23. The method of claim 13 further including comparing the first signal quality metric to a low-level response threshold and generating a low-level loss of signal quality response in response to the signal quality metric crossing the low-level response threshold.

24. The method of claim 13 further comprising determining a vector selection metric for each of the plurality of sensing vectors, selecting one or more sensing vectors based on a comparison of the vector selection metric to a vector selection threshold.

25. A computer readable medium for storing a set of instructions which cause a subcutaneously implanted medical device system to:
sense signals from a plurality of subcutaneous sensing vectors formed between a plurality of subcutaneous electrodes;
determine a signal quality metric for each of the subcutaneous sensing vector signals;
compare the signal quality metric for each subcutaneous sensing vector to a threshold; and
provide a loss of signal quality response in response to the signal quality metric crossing the threshold
wherein determining the signal quality metric comprises calculation of a characteristic of the vector signal, the characteristic corresponding to the quality of the vector signal for providing accurate separation of a sinus rhythm of a patient and an arrhythmia of the patient.

* * * * *